US006841668B2

United States Patent
Judd et al.

(10) Patent No.: US 6,841,668 B2
(45) Date of Patent: Jan. 11, 2005

(54) POLYOXOMETALATE CATALYSTS FOR THE PREPARATION OF STERICALLY HINDERED N-SUBSTITUTED ARYLOXYAMINES

(75) Inventors: Deborah Judd, Poughkeepsie, NY (US); Sai P. Shum, Jamesburg, NJ (US); Stephen D. Pastor, Danbury, CT (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 108 days.

(21) Appl. No.: 10/406,886

(22) Filed: Apr. 4, 2003

(65) Prior Publication Data

US 2003/0208071 A1 Nov. 6, 2003

Related U.S. Application Data

(60) Provisional application No. 60/371,899, filed on Apr. 11, 2002.

(51) Int. Cl.[7] .................... C07D 279/06; C07D 417/00; C07D 413/12; C07D 413/00; C07D 239/00
(52) U.S. Cl. ............................ 544/53; 544/55; 544/97; 544/113; 544/242; 546/187; 546/189; 546/191; 548/146; 548/215; 548/300.2; 548/542; 564/300
(58) Field of Search ............................ 544/97, 53, 55, 544/113, 242; 546/187, 189, 191; 548/146, 215, 300.1, 542; 564/300

(56) References Cited

U.S. PATENT DOCUMENTS 4,803,187 A    2/1989 Lyons et al. ................ 502/200

6,547,841 B2 * 4/2003 Pastor et al. ................ 44/275
6,579,328 B2 * 6/2003 Pastor et al. ................ 44/275

OTHER PUBLICATIONS

A. C. Scott, J. Chem. Soc., Perkin Trans. 2, (1980), pp. 260–266.
L. J. Beckwith et al., J. Chem. Soc., Chem. Commun. (1981), pp. 595–597.
R. Neumann, Prog. Inorg. Chem. (1998), 47, pp. 317–370.
Masahiro Sadakane et al., Chem. Rev. (Washington, D.C.) (1998), 98(1), pp. 219–237.
L. Kuznetsova et al., J. Mol. Cat. A: Chem. (1997), 117, pp. 389–396.
C. L. Hill et al., Coordination Chemistry Reviews (1995), 143, pp. 407–455.
C. Hill et al, Mol. Eng. (1993), 3(1–3), pp. 263–275.
M. Cramarossa et al., J. Mol. Catal. A: Chem. (1997), 127(1–3), pp. 85–94.
D. Duncan et al., J. Am. Chem. Soc. (1995), 117(2), pp. 681–691.
X. Zhang et al., Inorg. Chem. (2001), 40, pp. 418–419.
D. A. Judd et al., J. Am. Chem. Soc. (1997), 119, pp. 5461–5462.
V. Kogan et al., Angew. Chem. Int. Ed. (1999), 38, No. 22, pp. 3331–3334.

* cited by examiner

Primary Examiner—Mukund J. Shah
Assistant Examiner—Zachary C. Tucker
(74) Attorney, Agent, or Firm—Tyler A. Stevenson

(57) ABSTRACT

Sterically hindered N-substituted aryloxyamines are prepared by the Keggin polyoxometalate or the transition metal substituted polyoxometalate (TMS-POM) catalyzed decomposition of diazonium salts in the presence of a sterically hindered nitoxyl radical. These compounds are useful as thermal and light stabilizers for a variety of organic substrates.

13 Claims, No Drawings

POLYOXOMETALATE CATALYSTS FOR THE PREPARATION OF STERICALLY HINDERED N-SUBSTITUTED ARYLOXYAMINES

This application claims the benefit under 35 USC 119(e) of U.S. provisional app. No. 60/371,899, filed Apr. 11, 2002.

This invention pertains to a process for preparing sterically hindered N-substituted aryloxyamines by the catalytic decomposition of a diazonium salt in the presence of a sterically hindered nitroxyl radical using polyoxometalates of the Keggin class or transition metal substituted polyoxometalates of the Keggin class.

BACKGROUND OF THE INVENTION

N-Aryloxyamines have been prepared in the prior art by the reaction of a phenylhydrazine with a stable nitroxide. In certain instances, N-aryloxyamines have been prepared in low yield by the decomposition of aryldiazonium salts in the presence of a nitroxyl radical, but without a transition metal catalyst present. The focus of these papers is on mechanistic studies. The products are obtained in poor yields and the reaction is limited in scope. A. C. Scott et al., J. Chem. Soc., Perkin Trans. 2, 1980, 260–266.

Beckwith et al. reported the intramolecular addition of an aryl radical formed by decomposition of a diazonium salt to a double bond. The resultant alkyl radical is trapped by a stable nitroxyl radical. L. J. Beckwith and G. F. Meijs, J. Chem. Soc., Chem. Commun. 1981, 595–597.

In co-pending application Ser. No. 09/824,149, a transition metal-catalyzed process is disclosed for a commercially viable preparation of N-substituted aryloxyamines by the reaction of an aryldiazonium ion with a sterically hindered nitroxyl radical. The transition metals include copper(I), copper(II), cobalt(II), manganese(II), titanium(III), iron(II), iron(III), cobalt(III), nickel(II), gold(I) or chromium(III).

Surprisingly, the yield of aryloxyamine using the catalysts of the instant invention, for the reaction of aryldiazonium ions with sterically hindered nitroxyl radicals is equivalent to or greater than that for simple transition metal salts. This is especially surprising considering that concentration of the "transition metal" is significantly lower in the instant invention. For example application Ser. No. 09/824,149 demonstrates that the use of ferrous sulfate as a catalyst in the process to produce sterically hindered aryloxyamines results in a less than 50% yield. In the instant invention, the Fe(II) substituted polyoxometalate, $K_7PFe(II)W_{11}O_{39}$, results in a 72.7% isolated yield of the aryloxyamine. The percentage of transition metal of the polyoxometalate catalysts of the instant invention is much lower than the percentage of transition metal in the simple transition metals salts used in co-pending application Ser. No. 09/824,149, i.e. the Fe(II) substituted polyoxometalate contains only 1.85% iron compared to 20% iron in ferrous sulfate heptahydrate. Despite the lower concentration of transition metals in the polyoxometalate catalysts of the instant invention compared to the concentrations found in co-pending application Ser. No. 09/824,149, high yields are still obtained.

Polyoxometalates (POMs) are large metal oxide clusters of the early transition metals; tungsten(VI), molybdenum (VI), vanadium(V), niobium(V) or tantalum(V). POMs are formed by linking $MO_6$ octahedra together via either corner shared, edge shared or face shared linkages. The structure and catalytic properties of transition metal substituted polyoxometalates has been extensively reviewed (Neumann, Ronny, Prog. Inorg. Chem. (1998), 47 317–370.; Sadakane, Masahiro; Steckhan, Eberhard. Chem. Rev. (Washington, D.C.) (1998), 98(1), 219–237; L. I. Kuznetsova et al. *J. Mol. Cat. A: Chem.* 1997, 117, 389; C. L. Hill and M. Prosser-McCartha, Coordination Chemistry Reviews 1995 143, 407–455 and Hill, Craig L.; Kim, Gyu-Shik; Prosser-McCartha, Christina M.; Judd, Debbie. Mol. Eng. (1993), 3(1–3), 263–75). Other reports discussing the structure, synthesis, and applications of polyoxometalates include (a) Cramarossa, M. R et. al. J. Mol. Catal. A: Chem. (1997), 127(1–3), 85–94, which describes the homogeneous oxidation of cyclohexane and adamantane transition metal-modified, Keggin-type heteropoly complexes; (b) Lyons et al., in U.S. Pat. No. 4,803,187, which describes the use of POMs for the oxidation of alkanes to alcohols or ketones; (c) Duncan, Dean C.; Chambers, R. Carlisle; Hecht, Eric; Hill, Craig L. *J. Am. Chem. Soc.* (1995), 117(2), 681–91, which reports the mechanism of olefin epoxidation by hydrogen peroxide and $H_3[PW_{12}O_{40}]$; (d) X. Zhang et al. *Inorg. Chem.* 2001, 40, 418, which describes the use of $[(n-C_4H_9)_4N]_6$ $[Fe^{III}_4(H_2O)_2(PW_9O_{34})_2]$ for the oxidation of alkenes using hydrogen peroxide; and (e) D. A. Judd, et al. *J. Am. Chem. Soc.* 1997, 119, 5461, which reports the synthesis of $[P_2W_{12}(NbO_2)_6O_{56}]^{12-}$. These references in general describe oxidative applications of polyoxometalates unrelated to the instant invention. The use of polyoxometalates for the deoxygenation of aldehydes and ketones is described by V. Kogan *Angew. Chem. Int. Ed.* 1999, 38, 3331 and is unrelated to the instant invention.

It is clear that the instant invention provides an improved class of catalysts for the preparation of sterically hindered aryloxyamines described in co-pending application Ser. No. 09/824,149. The disclosure of U.S. application Ser. No. 09/824,149 is hereby incorporated by reference.

DETAILED DISCLOSURE

The instant invention pertains to a process for preparing a sterically hindered N-aryloxyamine of formula I, II, III, IV, V or VI

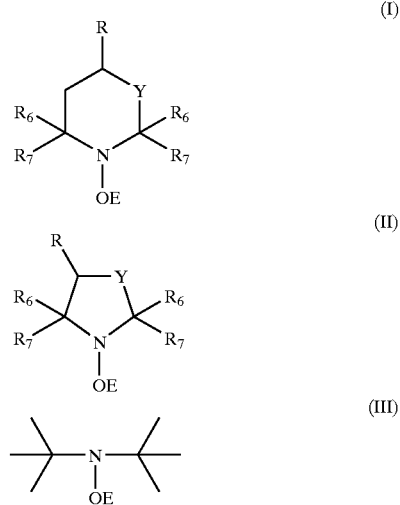

(IV)
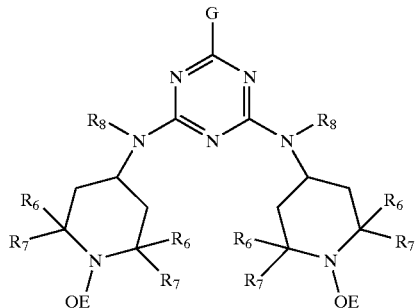

(V)
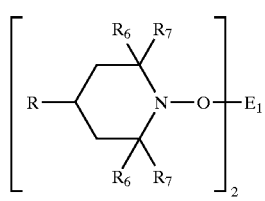

(VI)
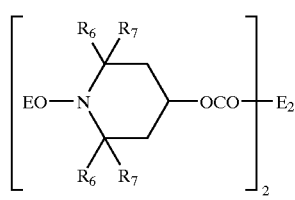

which process comprises reacting a sterically hindered nitroxyl compound of formula VII, VII, IX, X or XI (VII)
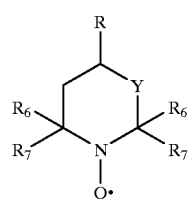

(VIII)
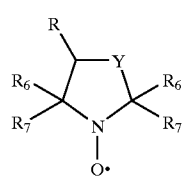

(IX)
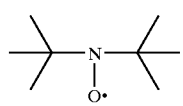

(X)
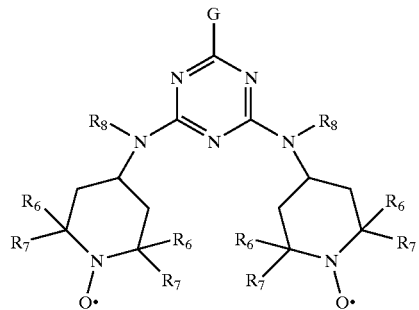

(XI)
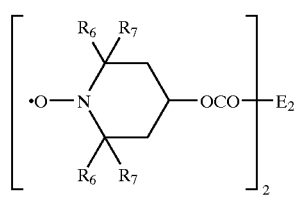

with a diazonium salt of an aromatic amine of formula XII, XIII or XIV (XII)
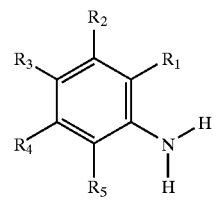

(XIII)
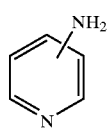

(XIV)
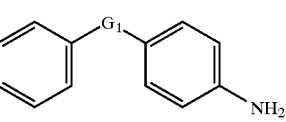

in the presence of a polyoxometalate of the Keggin class or a transition metal substituted polyoxometalate of the Keggin class, wherein Y is —CH$_2$—, —O—, —S— or —NR$_8$— where R$_8$ is hydrogen or alkyl of 1 to 12 carbon atoms, R$_6$ and R$_7$ are independently alkyl of 1 to 8 carbon atoms, or R$_6$ and R$_7$ together are tetramethylene or pentamethylene, E is 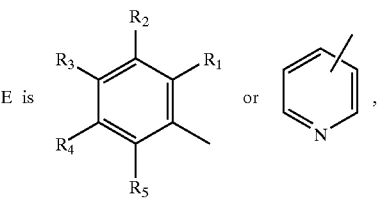 or 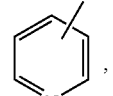, E₁ is 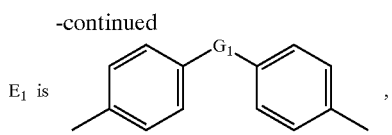, E₂ is alkylene of 2 to 12 carbon atoms,
G is chloro or —N(2-ethylhexyl)₂,
G₁ is —CH₂—, —CO— or —O—,
R is hydrogen, alkyl of 1 to 18 carbon atoms, aralkyl of 7 to 15 carbon atoms, aryl of 6 to 10 carbon atoms, hydroxyl, carboxyl, amino, alkylamino of 1 to 18 carbon atoms, dialkylamino of 2 to 36 carbon atoms, oxo, alkylthio of 1 to 18 carbon atoms, alkoxy of 1 to 18 carbon atoms, aryloxy of 7 to 15 carbon atoms, benzoyloxy, alkylcarbonyloxy of 2 to 18 carbon atoms or alkylcarbonylamino of 2 to 18 carbon atoms, and R₁ to R₅ are independently hydrogen, halogen, nitro, cyano, alkyl of 1 to 18 carbon atoms, aralkyl of 7 to 15 carbon atoms, aryl of 6 to 10 carbon atoms, hydroxyl, carboxyl, alkylthio of 1 to 18 carbon atoms, alkoxy of 1 to 18 carbon atoms, aryloxy of 7 to 15 carbon atoms, alkylcarbonyloxy of 1 to 18 carbon atoms, alkylsulfonyl of 1 to 18 carbon atoms, arylsulfonyl of 6 to 15 carbon atoms, sulfo or —P(O)(OH)₂ or —P(O)(OR₆)₂, or any two vicinal substituents connected together to form a mono or polycyclic ring, so that formula VII can represent inter alia 1-naphthylamine or 2-naphthylamine; or any two vicinal carboxyl groups can be joined to form an imide; or R₃ is 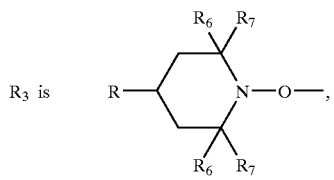, where R, R₆ and R₇ are as defined above.

The diazonium salt of the aromatic amine of formula VII can be prepared by reaction with an alkyl nitrite ester, such as tert-butyl nitrite. The diazonium salt can also be prepared using a nitrite salt and an acid, such as sodium nitrite and hydrochloric acid.

Indeed, the instant compounds can be made directly from nitroxides which are commercially available such as TEMPO (1-oxyl-2,2,6,6-tetramethylpiperidine), 4-OXOTEMPO (1-oxyl-2,2,6,6-tetramethyl-4-oxopiperidine) and di-tert-butyl nitroxide.

The reaction is conveniently carried out in acetonitrile as solvent at a temperature of between about 0 to about 100° C., for instance about 20 to about 70° C.

The present invention describes the use of polyoxometalates of the Keggin class, and "transition metal" substituted polyoxometalates (TMS-POM) of the Keggin class, where "transition metal" is defined as a d electron containing metal. The transition metals are for example selected from Ti, Cr, Mn, Fe, Co, Ni, Zn, Ru, Rh, Pd, Ag, Re, Os, Ir, Pt, Au, and Hg. Additionally, the present definition of "transition metal" is expanded to include the the P-block elements such as Al, Sn and Pb.

The Keggin structure is a heteropolyoxometalate with a general formula $[XM_{12}O_{40}]^{p-}$ where a central heteroatom is surrounded by twelve $MO_6$ octahedra. TMS-POMs are formed by removal of a $(M=O)^{4+}$ from the Keggin structure creating a "lacunary" Keggin $[XM_{11}O_{39}]^{(p+4)-}$ in the case where M is W(VI) or Mo(VI) and ligating the "transition metal" into the penta-coordinate hole formed.

The Keggin polyoxometalates and the transition metal substituted polyoxometalates (TMS-POMs) employed in the processes of this invention are of the general formula (1), $[XM_{12}O_{40}]^{p-}$ and (2), $[XM_{11}M'O_{39}]^{p-}$, respectively (1)

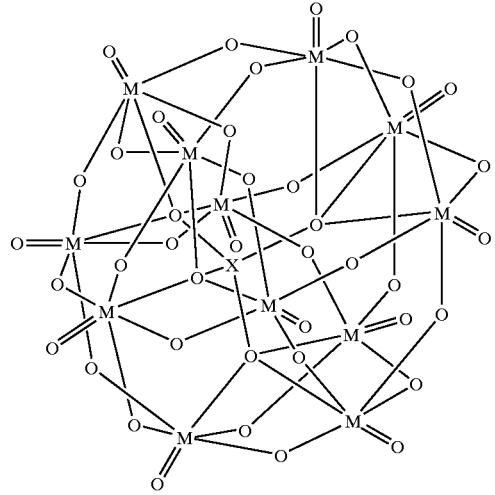

(2)

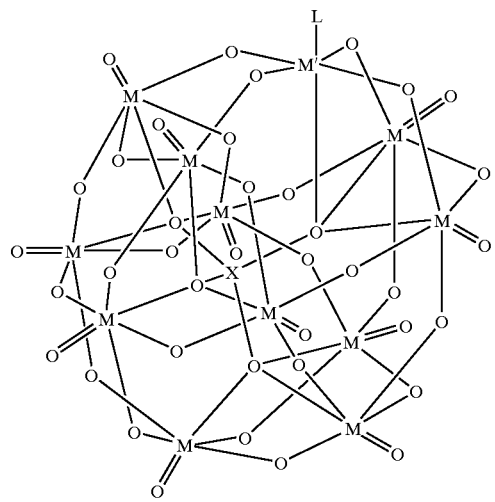

where
M is W(VI) or Mo(VI); or each M is independently selected from W(VI), Mo(VI), V(V), Nb(V) and Ta(V);
L is water;
M' is a transition metal of Group 4, 5, 6, 7, 8, 9, 10, 11 or 12, or is a metaloid selected from Al, Si, Ga, Ge, Sn, Sb, Te and Pb; and
X can be H, most nonmetal elements or most transition metals.

For example, M' is Ti, Cr, Mn, Fe, Co, Cu, Ni, Zn, Ru, Rh, Pd, Ag, Re, Os, Ir, Pt, Au, Hg, Al, Sn or Pb.

For example, M is W(VI) or Mo(VI); M' is Ti, Cr, Mn, Fe, Co, Ni, Cu, Zn or Al and X is P, Sn, Si, Ge, As, B, Al, Zn, Co, Fe, Ti, Zr and Ga; For instance M is W(VI), M' is Fe, Co or Cu and X is P.

M' is the "transition metal" that is substituted into the polyoxometalate of the Keggin class.

The definition "M is W(VI) or Mo(VI); or each M is independently selected from W(VI), Mo(VI), V(V), Nb(V) and Ta(V)" means that in formula (1) or (2), every M is W(VI), every M is Mo(VI), or each M is independently selected from from W(VI), Mo(VI), V(V), Nb(V) and Ta(V).

The coordination of water and other ligands to M' during preparation of the TMS-POM is well known and these products are within the scope of the instant invention. The polyoxometalates are large polyanions, with a negative charge of p. One skilled in the art can easily determine p from the oxidation states of X, M and M'; for example for $[P(V)W(VI)_{12}O_{40}]$ has a charge=$[5+6(12)-2(40)]=-3$; $[P(V)V(V)_2Mo(VI)_{10}O_{40}]$ has a charge=$[5+2(5)+10(6)-2(40)]=-5$; $[P(V)W(VI)_{11}Co(II)O_{39}]$ has a charge=$[5+11(6)+2-2(39)]=-5$. Due to the anionic charge on these clusters, cations are associated with them. The solubility of the polyoxometalates can be altered by the choice of counterion. The counterions can be but are not limited to any combination of the following: protons ($H^+$); alkali metals such as Li, Na, K, Rb, Cs; alkali earth metals such as Be, Mg, Ca, Sr; quarternary ammonium ions such as tetrabutylammonium, phosphonium ion, sulfonium ions, and the like.

The process is carried out in the presence of about 0.1 mole % to about stoichiometric quantities of the transition metal catalyst.

In another embodiment, Y is methylene.

In other embodiments, R is hydrogen, hydroxyl, oxo or acetamido.

For example, $R_1$ to $R_5$ are each hydrogen; or $R_1$ is nitro, $R_3$ is chloro or trifluoromethyl, and $R_2$, $R_4$ and $R_5$ are hydrogen; or $R_1$ and $R_3$ are bromo, and $R_2$, $R_4$ and $R_5$ are hydrogen.

In another embodiment, $R_6$ and $R_7$ are each methyl.

In another embodiment, $R_1$ and $R_3$ are each bromo or chloro.

A further aspect of this invention is the addition of pyridine to the reaction mixture either as a component of the reaction mixture or as the solvent. Pyridine has been found to further increase the yield of the reaction. In certain cases, pyridine has been found to have superior solvent properties. For example, when the diazonium salt is made using sodium nitrite and hydrochloric acid, pyridine also serves as a basic medium for neutralizing excess acid.

The stabilization of diazonium salts by pyridine has been reported by Heinrich Zollinger et al. (Helv. Chimica Acta, 59, 1438 (1976). Furthermore it is stated that pyridine promotes a homolytic radical pathway. Without a transition metal catalyst, however, the homolytic cleavage at 70° C. is slow and is not useful.

The instant invention also pertains to preparation of a stabilizing composition which comprises (a) an organic material subject to degradation by heat, light or oxygen, and (b) an effective stabilizing amount of a compound of formula I, II or III as described above.

For example, the organic material is a natural, semi-synthetic or synthetic polymer, especially a thermoplastic polymer.

In another embodiment, the polymer is a polyolefin or polycarbonate; for example, polyethylene or polypropylene; or is polypropylene; or the polymer is a styrenic, ABS, a nylon, a polyester such as poly(ethylene terephthalate) or poly(butylene terephthalate), a polyurethane, an acrylate, a rubber modified styrenic, poly(vinyl chloride), poly(vinyl butyral), polyacetal (polyoxymethylene), poly(ethylene naphthalenedicarboxylate), or other blends or copolymers such as poly(ethylene/1,4-cyclohexylenedimethylene terephthalate) PETG or an ionomer.

In another embodiment of the instant invention, the organic material is a resin selected from the group consisting of a thermoset acrylic melamine resin, an acrylic urethane resin, an epoxy carboxy resin, a silane modified acrylic melamine, an acrylic resin with carbamate pendant groups crosslinked with melamine or an acrylic polyol resin crosslinked with melamine containing carbamate groups.

For example, the resin is a thermoset acrylic melamine resin or an acrylic urethane resin.

In yet another embodiment of the instant invention, the organic material is a recording material.

The recording materials according to the invention are suitable for pressure-sensitive copying systems, photocopying systems using microcapsules, heat-sensitive copying systems, photographic materials and ink jet printing.

The recording materials according to the invention are distinguished by an unexpected improvement in quality, especially with regard to the fastness to light.

The recording materials according to the invention have the construction known for the particular use. They consist of a customary carrier, for example, paper or plastic film, which has been coated with one or more layers. Depending on the type of material, these layers contain the appropriate necessary components, in the case of photographic materials, for example, silver halide emulsions, dye couplers, dyes and the like. Material particularly suitable for ink jet printing has a layer particularly absorptive for ink on a customary carrier. Uncoated paper can also be employed for ink jet printing. In this case the paper acts at the same time as the carrier material and as the ink-absorbent layer. Suitable material for ink jet printing is, for example, described in U.S. Pat. No. 5,073,448, which is incorporated herein by reference.

The recording material can also be transparent as, for example, in the case of projection films.

The compounds of formula I, II, or III can be incorporated into the carder material as early as the production of the latter, in the production of paper, for example, being added to the paper pulp. A second method of application is to spray the carder material with an aqueous solution of compounds of formula I, II or III or to add the compounds to the coating composition.

Coating compositions intended for transparent recording materials suitable for projection cannot contain any particles which scatter light, such as pigments and fillers.

The dye-binding coating composition can contain a number of other additives, for example, antioxidants, light stabilizers (including also UV absorbers which do not fall under the scope of the UV absorbers of this invention), viscosity improvers, fluorescent brighteners, biocides and/or antistatic agents.

The coating composition is usually prepared as follows: the water-soluble components, for example, the binder, are dissolved in water and stirred together; the solid components, for example, fillers and other additives already described, are dispersed in this aqueous medium; and disperison is advantageously carried out by means of devices, for example, ultrasonic systems, turbine stirrers, homogenizers, colloid mills, bead mills, sand mills, high-speed stirrers and the like. The compounds of formula I, II or III can be easily incorporated into the coating composition.

The recording material according to this invention contains 1 to 5000 mg/m², or 50–1200 mg/m², of a compound of formula I, II or III.

As already mentioned, the recording materials according to the invention embrace a wide field. The compounds of formula I, II or III can, for example, be employed in pressure-sensitive copying systems. They can be introduced either into the paper in order to protect the microencapsulated dye precursors there from light, or into the binder of the developer layer in order to protect the dyes formed there.

Photocopying systems using light-sensitive microcapsules which are developed by means of pressure are described in U.S. Pat. Nos. 4,416,966; 4,483,912; 4,352,200; 4,535,050; 4,535,463; 4,551,407; 4,562,137 and 4,608,330; and also in EP-A 139,479; EP-A 162,664; EP-A 164,931; EP-A 237,024; EP-A 237,025 and EP-A 260,129. In all these systems, the compounds can be put into the dye-receiving layer. The compounds can, however, also be put into the donor layer in order to protect the color formers from light.

Photographic materials which can be stabilized are photographic dyes and layers containing such dyes or precursors thereof, for example, photographic paper and films. Suitable materials are, for example, described in U.S. Pat. No. 5,364,749 which is incorporated herein by reference. The compounds of formula I, II or III act here as a UV filter against electrostatic flashes. In color photographic materials, couplers and dyes are also protected against photochemical decomposition.

The instant compounds can be used for all types of color photographic materials. For example, they can be employed for color paper, color reversal paper, direct-positive color material, color negative film, color positive film, color reversal film and the like. They are used inter alia for photographic color material which contains a reversal substrate or form positives.

Color-photographic recording materials usually contain, on a support, a blue-sensitive and/or a green-sensitive and/or a red-sensitive silver halide emulsion layer and, if desired, a protection layer, with the instant compounds being, for instance, either in the green-sensitive or the red-sensitive layer or in a layer between the green-sensitive and the red-sensitive layer or in a layer on top of the silver halide emulsion layers.

The compounds of formula I, II or III can also be employed in recording materials based on the principles of photopolymerization, photoplasticization or the rupture of microcapsules, or in cases where heat-sensitive and light-sensitive diazonium salts, leuko dyes having an oxidizing agent or dye lactones having Lewis acids are used.

Furthermore, the instant compounds can be employed in recording materials for dye diffusion transfer printing, thermal wax transfer printing and non-matrix printing and for use with electrostatic, electrographic, electrophoretic, magnetographic and laser-electrophotographic printers and pen-plotters. Of the above, recording materials for dye diffusion transfer printing are useful, for example, as described in EP-A 507,734.

The instant compounds can also be employed in inks, for instance inks for ink jet printing, for example, as described in U.S. Pat. No. 5,098,477 which is incorporated herein by reference.

The compounds of this invention exhibit superior hydrolytic stability, handling and storage stability as well as good resistance to extractability when present in a stabilized composition.

The methodology to make the instant compounds is described in the prior art. The intermediates needed to make the instant compounds are largely items of commerce.

In general polymers which can be stabilized include
1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, for instance polyethylene and polypropylene, can be prepared by different, and especially by the following, methods:
   a) radical polymerization (normally under high pressure and at elevated temperature).
   b) catalytic polymerization using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerization medium. The catalysts can be used by themselves in the polymerization or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).
2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).
3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EM), LLDPE/EVA, LLDPE/EAA and alternating or random polyalkylene/carbon monoxide copolymers and mixtures thereof with other polymers, for example polyamides.
4. Hydrocarbon resins (for example $C_5$–$C_9$) including hydrogenated modifications thereof (e.g. tackifiers) and mixtures of polyalkylenes and starch.
5. Polystyrene, poly(p-methylstyrene), poly(α-methylstyrene).
6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.
7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.
8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.
9. Polymers derived from α,β-unsaturated acids and derivatives thereof such as polyacrylates and polymethacrylates; polymethyl methacrylates, polyacrylamides and polyacrylonitriles, impact-modified with butyl acrylate.
10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.
11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.
12. Homopolymers and copolymers of cyclic ethers such as polyalkylene glycols, polyethylene oxide, polypropylene oxide or copolymers thereof with bisglycidyl ethers.
13. Polyacetals such as polyoxymethylene and those polyoxymethylenes which contain ethylene oxide as a comonomer; polyacetals modified with thermoplastic polyurethanes, acrylates or MBS.
14. Polyphenylene oxides and sulfides, and mixtures of polyphenylene oxides with styrene polymers or polyamides.
15. Polyurethanes derived from hydroxyl-terminated polyethers, polyesters or polybutadienes on the one hand and aliphatic or aromatic polyisocyanates on the other, as well as precursors thereof.
16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).
17. Polyureas, polyimides, polyamide-imides and polybenzimidazoles.
18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.
19. Polycarbonates and polyester carbonates.
20. Polysulfones, polyether sulfones and polyether ketones.
21. Crosslinked polymers derived from aldehydes on the one hand and phenols, ureas and melamines on the other hand, such as phenol/formaldehyde resins, urea/formaldehyde resins and melamine/formaldehyde resins.
22. Drying and non-drying alkyd resins.
23. Unsaturated polyester resins derived from copolyesters of saturated and unsaturated dicarboxylic acids with polyhydric alcohols and vinyl compounds as crosslinking agents, and also halogen-containing modifications thereof of low flammability.
24. Crosslinkable acrylic resins derived from substituted acrylates, for example epoxy acrylates, urethane acrylates or polyester acrylates.
25. Alkyd resins, polyester resins and acrylate resins crosslinked with melamine resins, urea resins, polyisocyanates or epoxy resins.
26. Crosslinked epoxy resins derived from polyepoxides, for example from bisglycidyl ethers or from cycloaliphatic diepoxides.
27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.
29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.
31. Polysiloxanes such as the soft, hydrophilic polysiloxanes described, for example, in U.S. Pat. No. 4,259,467; and the hard polyorganosiloxanes described, for example, in U.S. Pat. No. 4,355,147.
32. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.
33. Radiation curable compositions containing ethylenically unsaturated monomers or oligomers and a polyunsaturated aliphatic oligomer.
34. Epoxymelamine resins such as light-stable epoxy resins crosslinked by an epoxy functional coetherified high solids melamine resin such as LSE-4103 (Monsanto).

In general, the compounds of the present invention are employed in from about 0.01 to about 5% by weight of the stabilized composition, although this will vary with the particular substrate and application. An advantageous range is from about 0.05 to about 3%, and especially 0.05 to about 1%. However, some high performance films or in UV absorbing layers of laminates such as those produced by coextrusion may contain from 5–15% by weight of the instant compounds. Concentrations of 5–10% by weight are typical in certain coextrusion applications.

The stabilizers of the instant invention may readily be incorporated into the organic polymers by conventional techniques, at any convenient stage prior to the manufacture of shaped articles thereof. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain from about 0.01 to about 5%, for example from about 0.025 to about 2%, for instance from about 0.1 to about 1% by weight of various conventional additives, such as the materials listed below, or mixtures thereof.

1. Antioxidants
1.1. Alkylated monophenols, for example,
2,6-di-tert-butyl-4-methylphenol
2-tert-butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-($\alpha$-methylcyclohexyl)-4,6-dimethylphenol
2,6-di-octadecyl-4-methylphenol
2,4,6-tri-cyclohexylphenol
2,6-di-tert-butyl-4-methoxymethylphenol
1.2. Alkylated hydroquinones, for example,
2,6-di-tert-butyl-4-methoxyphenol
2,5-di-tert-butyl-hydroquinone
2,5-di-tert-amyl-hydroquinone
2,6-diphenyl-4-octadecyloxyphenol
1.3. Hydroxylated thiodiphenyl ethers, for example,
2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)
1.4. Alkylidene-bisphenols, for example,
2,2'-methylene-bis-(6-tert-butyl-4-methylphenol)
2,2'-methylene-bis-(6-tert-butyl-4-ethylphenol)
2,2'-methylene-bis-[4-methyl-6-($\alpha$-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-($\alpha$-methylbenzyl)-4-nonylphenol]
2,2'-methylene-bis-[6-($\alpha,\alpha$-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl)-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl]terephthalate.
1.5. Benzyl compounds, for example,
1,3,5-tri-(3,5-di-tert-butyl-4-hydroxybenzyl)-2,4,6-trimethylbenzene
di-(3,5-di-tert-butyl-4-hydroxybenzyl)sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl)isocyanurate
1,3,5-tris-(4-tert-butyl-3-hydroxy-2,6-dimethylbenzyl) isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt
1.6. Acylaminophenols, for example,
4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate
1.7. Esters of $\beta$-(3,5-di-tert-butyl-4-hydroxyphenyl)-propionic acid with monohydric or polyhydric alcohols, for example,

| | |
|---|---|
| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |
| triethanolamine | triisopropanolamine |

1.8. Esters of $\beta$-(5-tert-butyl-4-hydroxy-3-methylphenyl)-propionic acid with monohydric or polyhydric alcohols, for example,

| | |
|---|---|
| methanol | diethylene glycol |
| octadecanol | triethylene glycol |

| | |
|---|---|
| 1,6-hexanediol | pentaerythritol |
| neopentyl glycol | tris-hydroxyethyl isocyanurate |
| thiodiethylene glycol | di-hydroxyethyl oxalic acid diamide |
| triethanolamine | triisopropanolamine |

1.9. Amides of β-(3,5-di-tert-butyl-4-hydroxyphenyl)-propionic acid for example,
N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine 1.10 Diarylamines, for example,
diphenylamine, N-phenyl-1-naphthylamine, N-(4-tert-octylphenyl)-1-naphthylamine, 4,4'-di-tert-octyl-diphenylamine, reaction product of N-phenylbenzylamine and 2,4,4-trimethylpentene, reaction product of diphenylamine and 2,4,4-trimethylpentene, reaction product of N-phenyl-1-naphthylamine and 2,4,4-trimethylpentene.

2. UV absorbers and light stabilizers 2.1. 2-(2'-Hydroxyphenyl)-benzotriazoles, for example, the 5'-methyl-, 3',5'-di-tert-butyl-, 5'-tert-butyl, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxy-octa-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5. Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl)sebacate, bis-(1,2,2,6,6-pentamethylpiperidyl)sebacate, n-butyl-3,5-di-tert.butyl-4-hydroxybenzyl malonic acid bis-(1,2,2,6,6-pentanemethylpiperidyl)ester, condensation product of 1-hydroxyethyl-2,2,6,6-tetramethyl-4-hydroxypiperidine and succinic acid, condensation product of N,N'-(2,2,6,6-tetra-methylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl) 1,2,3,4-butanetetracarboxylate, 1,1'(1,2-ethanediyl)-bis-(3,3,5,5-tetramethylpiperazinone), bis(1-octyloxy-2,2,6,6-tetramethylpiperidin-4-yl)sebacate.

2.7. Oxalic acid diamides, for example, 4,4'-di-octyloxy-oxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis(3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy- as well as of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxy-ethoxy)phenyl]-6-(4-chlorophenyl)-s-triazine; 2,4-bis[2-hydroxy-4-(2-hydroxy-4-(2-hydroxy-ethoxy)phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloyl-hydrazine, N,N'-bis-salicyloylhydrazine, N,N'-bis-(3,5-di-tert-butyl-4-hydroxyphenylpropionyl)-hydrazine, 3-salicyloylamino-1,2,4-triazole, bis-benzylidene-oxalic acid dihydrazide.

4. Phosphites and Phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecyl-pentaerythritol diphosphite, di-(2,4,6-tri-tert-butylphenyl)-pentaerythritol diphosphite, di-(2,4-di-tert-butyl-6-methylphenyl)-pentaerythritol diphosphite, di-(2,4-di-tert-butylphenyl)pentaerythritol diphosphite, tristearyl-sorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.
8. Amine Oxides, for example, tridecyl amine oxide, tridodecyl amine oxide, trihexadecyl amine oxide, tri($C_{12}$–$C_{14}$ alkyl)amine oxide, tri($C_{16}$–$C_{18}$ alkyl)amine oxide, tri($C_{20}$–$C_{22}$ alkyl)amine oxide, di($C_{12}$–$C_{14}$ alkyl)methyl amine oxide, di($C_{16}$–$C_{18}$ alkyl)methyl amine oxide, di($C_{20}$–$C_{22}$ alkyl)methyl amine oxide, di(tallow alkyl)methyl amine oxide, di(coco alkyl)methyl amine oxide.
9. Polyamide stabilizers, for example copper salts in combination with iodides and/or phosphorus compounds and salts of divalent manganese.
10. Basic co-Stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.
11. Nucleating agents, for example, 4-tert-butyl-benzoic acid, adipic acid, diphenylacetic acid.
12. Fillers and reinforcing agents, for example, calcium carbonate, silicates, glass fibers, asbestos, talc, kaolin, mica, barium sulfate, metal oxides and hydroxides, carbon black, graphite.
13. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.
14. Benzofuranones and indolinones, for example those disclosed in U.S. Pat. Nos. 4,325,863, 4,338,244 or U.S. Pat. No. 5,175,312, or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl) benzofuran-2-one], 5,7-di-tert-butyl-3-(4-ethoxyphenyl) benzo-furan-2-one, 3-(4-acetoxy-3,5-dimethylphenyl)-5,7-di-tert-butyl-benzofuran-2-one, 3-(3,5-di-methyl-4-pivaloyloxyphenyl)-5,7-di-tert-butyl-benzofuran-2-one.

The co-stabilizers, with the exception of the benzofuranones listed under 14, are added for example in concentrations of 0.01 to 10%, relative to the total weight of the material to be stabilized.

Further compositions comprise, in addition to components (a) and (b) further additives, such as phenolic antioxidants, light stabilizers or processing stabilizers.

These additives are phenolic antioxidants (item 1 of the list), sterically hindered amines (item 2.6 of the list), phosphites and phosphonites (item 4 of the list), UV absorbers (item 2 of the list) and peroxide-destroying compounds (item 5 of the list).

Additional additives (stabilizers) which are also the benzofuran-2-ones, such as described, for example, in U.S. Pat. Nos. 4,325,863, 4,338,244 or U.S. Pat. No. 5,175,312.

For examples, the phenolic antioxidant is selected from the group consisting of n-octadecyl 3,5-di-tert-butyl-4-hydroxyhydrocinnamate, neopentanetetrayl tetrakis(3,5-di-tert-butyl-4-hydroxyhydrocinnammate), di-n-octadecyl3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl) benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocyanurate, 1,1,3,-tris(2-methyl-4-hydroxy-5-tert-butylphenyl)butane, 1,3,5-tris-[2-(3,5-di-tert-butyl-4-hydroxyhydrocinnamoyloxy) ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl3,5-di-tert-butyl-4-hydroxybenzyl-phosphonate), ethylene bis[3,3-di(3-tert-butyl-4-hydroxyphenyl)butyrate], octyl3,5-di-tert-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)-ethyl]-oxamide.

Another embodiment is the phenolic antioxidant which is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris(3,5-di-tert-butyl-4-hydroxybenzyl)isocyanurate, 2,6-di-tert-butyl-p-cresol or 2,2'-ethylidene-bis(4,6-di-tert-butylphenol).

The hindered amine compound is selected from the group consisting of bis(2,2,6,6-tetramethylpiperidin-4-yl)sebacate, bis(1,2,2,6,6-pentamethylpiperidin-4-yl)sebacate, di(1,2,2,6,6-pentamethylpiperidin-4-yl)(3,5-di-tert-butyl-4-hydroxybenzyl)butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4-yl) nitrilotriacetate, 1,2-bis(2,2,6,6-tetramethyl-3-oxopiperazin-4-yl)ethane, 2,2,4,4-tetramethyl-7-oxa-3,20-diaza-21-oxodispiro[5.1.11.2] heneicosane, polycondensation product of 2,4-dichloro-6-tert-octylamino-s-triazine and 4,4'-hexamethylenebis (amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylenebis-(amino-2,2,6,6-tetramethylpiperidine) and 1,2-dibromoethane, tetrakis(2,2,6,6-tetramethylpiperidin-4-yl)1,2,3,4-butanetetracarboxylate, tetrakis(1,2,2,6,6-pentamethylpiperidin-4-yl)1,2,3,4-butanetetracarboxylate, polycondensation product of 2,4-dichloro-6-morpholino-s-triazine and 4,4'-hexamethylenebis(amino-2,2,6,6-tetramethylpiperidine), N, N',N", N'"-tetrakis[(4,6-bis(butyl-1,2,2,6,6-pentamethylpiperidin-4-yl)-amino-s-triazin-2-yl]-1,10-diamino-4,7-diazadecane, mixed [2,2,6,6-tetramethylpiperidin-4-yl/β,β,β',β'-tetramethyl-3,9-(2,4,8,10-tetraoxaspiro[5.5]-undecane)diethyl]1,2,3,4-butanetetracarboxylate, mixed [1,2,2,6,6-pentamethylpiperidin-4-yl/β,β, β',β'-tetramethyl-3,9-(2,4,8,10-tetraoxaspiro[5.5]undecane)diethyl]1,2,3,4-butanetetracarboxylate, octamethylene bis(2,2,6,6-tetramethylpiperidin-4-carboxylate), 4,4'-ethylenebis(2,2,6,6-tetramethylpiperazin-3-one), N-2,2,6,6-tetramethylpiperidin-4-yl-n-dodecylsuccinimide, N-1,2,2,6,6-pentamethylpiperidin-4-yl-n-dodecylsuccinimide, N-1-acetyl-2,2,6,6-tetramethylpiperidin-4-yln-dodecylsuccinimide, 1-acetyl3-dodecyl-7,7,9,9-tetramethyl-1,3,8-triazaspiro[4.5]decane-2,4-dione, di-(1-octyloxy-2,2,6,6-tetramethylpiperidin-4-yl)sebacate, di-(1-cyclohexyloxy-2,2,6,6-tetramethylpiperidin-4-yl)succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-

(1-cyclohexyloxy-2,2,6,6-tetramethyl-piperidin-4-yl) imino], and 2,4,6-tris[N-(1-cyclohexyloxy-2,2,6,6-tetramethylpiperidin-4-yl)-n-butylamino]-s-triazine.

Another hindered amine compound is bis(2,2,6,6-tetramethylpiperidin-4-yl)sebacate, bis(1,2,2,6,6-pentamethylpiperidin-4-yl)sebacate, di(1,2,2,6,6-pentamethylpiperidin-4-yl)(3,5-di-tert-butyl-4-hydroxybenzyl)butylmalonate, the polycondensation product of 1-(2-hydroxyethyl)-2,2,6,6-tetramethyl-4-hydroxypiperidine and succinic acid, the polycondensation product of 2,4-dichloro-6-tert-octylamino-s-triazine and 4,4'-hexamethylenebis(amino-2,2,6,6-tetramethylpiperidine), N,N',N'',N'''-tetrakis[(4,6-bis(butyl-(1,2,2,6,6-pentamethylpiperidin-4-yl)amino)-s-triazine-2-yl]-1,10-diamino-4,7-diazadecane. di-(1-octyloxy-2,2,6,6-tetramethylpiperidin-4-yl)sebacate, di-(1-cyclohexyloxy-2,2,6,6-tetramethylpiperidin-4-yl)succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-(1-cyclohexyloxy-2,2,6,6-tetramethylpiperidin-4-yl)imino], or 2,4,6-tris[N-(1-cyclohexyloxy-2,2,6,6-tetramethyl-piperidin-4-yl)-n-butylamino]-s-triazine.

The instant composition can additionally contain another UV absorber selected from the group consisting of the benzotriazoles, s-triazines, the oxanilides, the hydroxybenzophenones, benzoates and the α-cyanoacrylates.

The instant composition may additionally contain an effective stabilizing amount of at least one other 2-hydroxyphenyl-2H-benzotriazole; another tris-aryl-s-triazine; or hindered amine or mixtures thereof.

The 2-hydroxyphenyl-2H-benzotriazole is selected from the group consisting of 2-(2-hydroxy-3,5-di-tert-amylphenyl)-2H-benzotriazole;
2-[2-hydroxy-3,5-di(α,α-dimethylbenzyl)phenyl]-2H-benzotriazole;
2-[2-hydroxy-3-(α,α-dimethylbenzyl)-5-tert-octylphenyl]-2H-benzotriazole;
2-{2-hydroxy-3-tert-butyl-5-[2-(omega-hydroxy-octa(ethyleneoxy)carbonyl)ethyl]phenyl}-2H-benzotriazole;
5-chloro-2-(2-hydroxy-3,5-di-tert-butylphenyl)-2H-benzotriazole;
5-chloro-2-(2-hydroxy-3-tert-butyl-5-methylphenyl)-2H-benzotriazole;
2-(2-hydroxy-5-tert-octylphenyl)-2H-benzotriazole; and
2-{2-hydroxy-3-tert-butyl-5-[2-(octyloxy)carbonyl)ethyl]phenyl}-2H-benzotriazole.

The other tris-aryl-s-triazine is selected from the group consisting of 2,4-bis(2,4-dimethylphenyl)-6-(2-hydroxy-4-octyloxyphenyl)-s-triazine;
2,4-diphenyl-6-(2-hydroxy-4-hexyloxyphenyl)-s-triazine;
2,4-bis(2,4-dimethylphenyl)-6-[2-hydroxy-4-(3-do-/tridecyloxy-2-hydroxypropoxy)phenyl]-s-triazine; and
2-(2-hydroxyethylamino)-4,6-bis[N-butyl-N-(1-cyclohexyloxy-2,2,6,6-tetramethylpiperidin-4-yl)amino]-s-triazine.

The alkyd resin lacquers which can be stabilized against the action of light and moisture in accordance with the instant invention are the conventional stoving lacquers which are used in particular for coating automobiles (automobile finishing lacquers), for example lacquers based on alkyd/melamine resins and alkyd/acrylic/melamine resins (see H. Wagner and H. F. Sarx, "Lackkunstharze" (1977), pages 99–123). Other crosslinking agents include glycouril resins, blocked isocyanates or epoxy resins.

The lacquers stabilized in accordance with the invention are suitable both for metal finish coatings and solid shade finishes, such as in the case of retouching finishes, as well as various coil coating applications. The lacquers stabilized in accordance with the invention are applied in the conventional manner by two methods, either by the single-coat method or by the two-coat method. In the latter method, the pigment-containing base coat is applied first and then a covering coat of clear lacquer over it.

It is also to be noted that the compounds of the present invention are applicable for use in non-acid catalyzed thermoset resins such as epoxy, epoxy-polyester, vinyl, alkyd, acrylic and polyester resins, optionally modified with silicon, isocyanates or isocyanurates. The epoxy and epoxy-polyester resins are crosslinked with conventional crosslinkers such as acids, acid anhydrides, amines and the like. Correspondingly, the epoxide may be utilized as the crosslinking agent for various acrylic or polyester resin systems that have been modified by the presence of reactive groups on the backbone structure.

When used in two-coat finishes, the compounds of the instant invention can be incorporated in the clear coat or both in the clear coat and in the pigmented base coat.

When water-soluble, water miscible or water dispersible coating are desired ammonium salts of acid groups present in the resin are formed. Powder coating composition can be prepared by reacting glycidyl methacrylate with selected alcohol components.

The instant benzotriazoles are made by conventional methods for preparing such compounds. The usual procedure involves the diazotization of a substituted o-nitroaniline followed by coupling the resultant diazonium salt with a substituted phenol and reduction of the azobenzene intermediate to the corresponding desired benzotriazole. The starting materials for these benzotriazoles are largely items of commerce or can be prepared by normal methods of organic synthesis.

While the instant benzotriazoles with their enhanced durability are particularly suited for automotive coating applications, it is contemplated that they will also be espeically useful in other applications where their enhanced durability is required such as in solar films and the like.

Some specific compounds which may be prepared include (i) 1-(2-nitro-4-trifluoromethylphenoxy)-2,2,6,6-tetramethylpiperidine;
(ii) 1-(2-nitro-4-chlorophenoxy)-2,2,6,6-tetramethylpiperidine;
(iii) 1-(2,4-dibromophenoxy)-2,2,6,6-tetramethylpiperidine;
(iv) 1-(2,4-dibromophenoxy)-4-hydroxy-2,2,6,6-tetramethylpiperidine;
(v) 1-(2,4-dibromophenoxy)-4-acetamido-2,2,6,6-tetramethylpiperidine;
(vi) 1-(2,4-dibromophenoxy)-4-oxo-2,2,6,6-tetramethylpiperidine;
(vii) 1-(2-naphthyloxy)-2,2,6,6-tetramethylpiperidine;
(viii) 1-(4-benzoylphenoxy)-2,2,6,6-tetramethylpiperidine;
(ix) 1-phenoxy-4-benzoyloxy-2,2,6,6-tetramethylpiperidine;
(x) N-phenoxy-di-tert-butylamine;
(xi) 2,4-bis[N-butyl-N-(1-phenoxy-2,2,6,6-tetramethylpiperidin-4-yl)amino]-6-chloro-s-triazine;
(xii) 2,4-bis{N-butyl-N-[1-(2,4-dibromophenoxy)-2,2,6,6-tetramethylpiperidin-4-yl]amino}-6-[N,N-bis(2-ethylhexyl)amino]-s-triazine;

(xiii) 2,4-bis[N-butyl-N-(1-phenoxy-2,2,6,6-tetramethylpiperidin-4-yl)amino]-6-[N,N-bis(2-ethylhexyl)amino]-s-triazine;
(xiv) 1-(3,5-di-tert-butylphenoxy)-2,2,6,6-tetramethylpiperidine;
(xv) 1-(pyridin-3-yloxy)-2,2,6,6-tetramethylpiperidine;
(xvi) 1-(2-nitro-4-chlorophenoxy)-2,2,6,6-tetramethyl-4-hydroxypiperidine;
(xvii) 4,4'-bis(2,2,6,6-tetramethylpiperidin-1-yloxy)benzophenone;
(xviii) di(1-phenoxy-2,2,6,6-tetramethyl-piperidin-4-yl)sebacate;
(xix) 5-[4-(2,2,6,6-tetramethylpiperidin-1-yloxy)-phenyl]-2-(2-hydroxy-3-$\alpha$-cumyl-5-tert-octylphenyl)-2H-benzotriazole;
(xx) 4,4'-bis[(4-hydroxy-2,2,6,6-tetramethylpiperidin-1-yl)oxy]diphenylmethane, or
(xxi) 1-(phthalimid-4-yloxy)-4-hydroxy-2,2,6,6-tetramethylpiperidine.

The following examples are for illustrative purposes only and are not to be construed to limit the scope of the invention in any manner whatsoever.

EXAMPLE 1
Synthesis of the Iron Substituted Keggin

A solution of the lacunary polyoxometalate $K_7PW_{11}O_{39}$ where one "W=O" is removed from phosphotungstic acid is prepared as follows: Phosphotungstic acid (15 g, 0.0052 mol) obtained from Aldrich is dissolved in water (35 ml). The resulting solution has a pH less than 1. The pH is raised to 5.2 by the addition of a 25 w/w % aqueous solution of potassium bicarbonate. The reaction mass is then heated to 70° C. Iron is substituted into the lacunary POM by addition of a ferrous sulfate (1.45 g, 0.005 mol in 10 ml water) solution the solution of "PW11" (pH~5) and continued to be heated for an additional 30 minutes. KCl (5 g) is added. MeOH is added and the reaction mass is put in the refrigerator. A yellow solid is obtained (8.6 g). IR is consistent with the desired compound. Water by Karl-Fischer analysis indicated ~11 waters are present. Elemental indicated that some impurities are present. Elemental $KH_4PW_{11}O_{39}Fe$—$OH_2$ 10 $H_2O$ 0.3 KCl 0.5 HCl actual (theoretical): K 1.6 (1.69); H 0.9 (0.89); P 0.42 (1.02)*; W 64 (67); Fe 1.6 (1.85); O (by difference) 30.7 (26.5); it is not uncommon for the phosphorous to appear low when analyzed by gravimetric analysis due to incomplete degradation of the cage.

EXAMPLE 2
Synthesis of the Cobalt Substituted Keggin. (Inorganic Chemistry 2000 39(17), 3828–3837; J. Mol. Catal. A: Chem. 1997 117, 390.)

A solution of the lacunary polyoxometalate $Na_7PW_{11}O_{39}$ where one W=O is removed from phosphotungstic acid is prepared as follows: Phosphotungstic acid (37.5 g, 0.013 mol) obtained from Aldrich is dissolved in water (175 ml). The resulting solution has a pH less than 1. Phosphoric acid is added (0.14 g of 85%). A 10 w/w % aqueous solution of sodium hydroxide is added to raise the pH to ~4. Cobalt is substituted into the lacunary POM by addition of a cobalt nitrate (3.78 g, 0.013 mol in 25 ml water) solution the solution of "PW11" (pH~3). 2 N HCl is added to lower the pH to ~2. The reaction mass is then heated to 80° C. for ~2 hours. KCl (25 g) is added. A column is filled with Amberlyst 15 ion exchange resin. The column is neutralized with KOH to exchange the potassium ions for proton. The aqueous solution of the "PW11Co" is passed through the column. A lilac purple solid (36.5 g) is obtained by concentrating the aqueous solution on a rotary evaporator until a purple solid starts to form and cooling to room temperature. IR is consistent with the desired compound. Elemental analysis indicates that the catalyst is very impure and contains significant amounts of KCl and some $KNO_3$. Elemental analysis: K 15.87; H 0.39; P 0.64; W 39.15; Co 0.973; Cl 11.8; N 0.67; C 0.09. The ratio of P/Co/W is consistent with the desired compound. The catalyst was used as is.

EXAMPLE 3

Synthesis of the Copper Substituted Keggin; (Inorganic Chemistry 2000 39(17), 3828–3837; J. Mol. Catal. A: Chem. 1997 117, 390.)

A solution of the lacunary polyoxometalate $Na_7PW_{11}O_{39}$ where one "W=O" is removed from phosphotungstic acid is prepared as follows: Phosphotungstic acid (37.5 g, 0.013 mol) obtained from Aldrich is dissolved in water (175 ml). The resulting solution has a pH less than 1. Phosphoric acid is added (0.14 g of 85%). A 10 w/w % aqueous solution of sodium hydroxide is added to raise the pH to ~4. Cobalt is substituted into the lacunary POM by addition of a copper nitrate (3.02 g, 0.013 mol in 25 ml water) solution the solution of "PW11" (pH~3). 2 N HCl is added to lower the pH to ~2. The reaction mass is then heated to 80° C. for ~2 hours. KCl (25 g) is added. A column is filled with Amberlyst 15 ion exchange resin. The column is neutralized with KOH to exchange the protons on the column for potassium. The aqueous solution of the "PW11Cu" is passed through the column. A green-gray solid (54.3 g) is obtained by concentrating the aqueous solution on a rotary evaporator until a solid starts to form and cooling to room temperature. Product must be impure >100% yield obtained. IR is consistent with the desired compound. Elemental analysis indicates that the catalyst is very impure and contains significant amounts of KCl and some $KNO_3$. Elemental analysis: K 22.3; H 0.3; P 0.6; W 33.9; Cu 1.2. The ratio of P/Co/W is consistent with the desired compound. The catalyst was used as is.

EXAMPLE 4

Synthesis of Mixed Addenda Keggin $H_5PV_2Mo_{10}O_{40}$ (J. Gen. Chem. USSR 1954 24, 697).

Sodium metavanadate (15 g), phosphoric acid (1.7 ml of 85%) and molybdenum oxide (37 g) are refluxed in 400 ml of water for 8 hours. The reaction mass is acidified with concentrated HCl (72.5 ml). The reaction mass is extracted with ether (100 ml). The ether layer is collected and the ether is evaporated under air. IR is consistent with the desired compound. Elemental analysis: H 1.1; P 1.7; Mo 49.5; V 5.4; Na 0.2. The ratio of P/V/Mo is consistent with the desired compound. $^{31}$P-NMR consistent with desired compound. The monosubstituted analogue is present [$PVMo_{11}O_{40}$]. The catalyst was used as is.

EXAMPLE 5

1-Phenoxy-2,2,6,6-tetramethylpiperidine (1.0 Mole % Fe Polyoxometalate Based Nitroxyl; 2 Molar Excess Aniline)

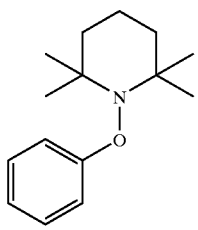

To a suspension of 1.95 g (12.5 mmol) of 2,2,6,6-tetramethylpiperidine-1-oxyl, 3.09 g (30.0 mmol) of tert-butylnitrite and 378 mg (~0.125 mmol) of iron polyoxometallate ($K_7PFeW_{11}O_{39} \cdot H_2O$) in 100 mL of pyridine at 70° C. under a nitrogen atmosphere is added dropwise over 5 minutes 2.32 g (25 mmol) of aniline in 5 mL of pyridine. Evolution of gas is observed during the addition of aniline. The dark red reaction mixture is kept at 70° C. until evolution of gas subsided. Upon cooling to ambient temperature, the reaction mixture is then concentrated to an thick oil. The residue is purified by vacuum flash chromatography (heptane) to give 2.10 g of a colorless oil in 72.2% yield: $^1H$ NMR ($CDCL_3$) (300.08 MHz) d 1.42, 1.29, 1.12 (overlapping m, $CH_2$, 6 H), 1.16 (s, $CH_3$, 6 H), 1.017 (s, $CH_3$, 6 H), 7.25 (d, CH, 2H, $^3JHH'=8.2$ Hz), 7.12 (dd, CH, 2H, $^3JHH'=8.3$ Hz, $^3JHH'=8.2$ Hz), 6.78 (tt, CH, 1 H, $^3JHH'=7.2$ Hz, $^4JHH''=1.2$ Hz); MS [M+1]234.

EXAMPLE 6
1-Phenoxy-2,2,6,6-tetramethylpiperidine (1.0 Mole % Co Polyoxometallate Based Nitroxyl; 2 Molar Excess Aniline)

The procedure of Example 5 is repeated using 1.95 g (12.5 mmol) of 2,2,6,6-tetramethylpiperidine-1-oxyl, 3.09 g (30.0 mmol) of tert-butylnitrite and 378 mg (~0.125 mmol) of cobalt polyoxometallate ($K_7PCoW_{11}O_{39} \cdot H_2O$) in 100 mL of pyridine and 2.32 g (25 mmol) of aniline in 5 mL of pyridine. The crude is purified by vacuum flash chromatography (heptane) to give 2.12 g of a colorless oil in 72.8% yield.

EXAMPLE 7
1-Phenoxy-2,2,6,6-tetramethylpiperidine (1.0 Mole % Cu Polyoxometallate Based Nitroxyl; 2 Molar Excess Aniline)

The procedure of Example 5 is repeated using 1.95 g (12.5 mmol) of 2,2,6,6-tetramethylpiperidine-1-oxyl, 3.09 g (30.0 mmol) of tert-butylnitrite and 379 mg (~0.125 mmol) of copper polyoxometallate ($K_7PCuW_{11}O_{39} \cdot H_2O$) in 100 mL of pyridine and 2.32 g (25 mmol) of aniline in 5 mL of pyridine. The crude is purified by vacuum flash chromatography (heptane) to give 2.41 g of a colorless oil in 82.8% yield.

EXAMPLE 8
1-Phenoxy-2,2,6,6-tetramethylpiperidine (2.0 Mole % Cu Polyoxometallate Based Nitroxyl; 2 Molar Excess Aniline)

The procedure of Example 5 is repeated using 1.95 g (12.5 mmol) of 2,2,6,6-tetramethylpiperidine-1-oxyl, 3.09 g (30.0 mmol) of tert-butylnitrite and 758 mg (~0.25mmol) of copper polyoxometallate ($K_7PCuW_{11}O_{39} \cdot H_2O$) in 100 mL of pyridine and 2.32 g (25 mmol) of aniline in 5 mL of pyridine. The crude is purified by vacuum flash chromatography (heptane) to give 2.52 g of a colorless oil in 82.8% yield.

EXAMPLE 9
1-Phenoxy-2,2,6,6-tetramethylpiperidine (10.0 Mole % Cu polyoxo-metallate Based Nitroxyl; 2 Molar Excess Aniline)

The procedure of Example 5 is repeated using 1.95 g (12.5 mmol) of 2,2,6,6-tetramethylpiperidine-1-oxyl, 3.09 g (30.0 mmol) of tert-butylnitrite and 3790 mg (~1.25 mmol) of copper polyoxometallate ($K_7PCuW_{11}O_{39} \cdot H_2O$) in 100 mL of pyridine and 2.32 g (25 mmol) of aniline in 5 mL of pyridine. The crude is purified by vacuum flash chromatography (heptane) to give 2.55 g of a colorless oil in 87.6% yield.

EXAMPLE 10
1-Phenoxy-2,2,6,6-tetramethylpiperidine (1.0 Mole % V Polyoxometallate Based Nitroxyl; 2 Molar Excess Aniline)

The procedure of Example 5 is repeated using 1.95 g (12.5 mmol) of 2,2,6,6-tetramethylpiperidine-1-oxyl, 3.09 g (30.0 mmol) of tert-butylnitrite and 217 mg (~0.125 mmol) of vanadium polyoxometallate ($H_5PV_2Mo_{10}O_{40}$) in 100 mL of pyridine and 2.32 g (25 mmol) of aniline in 5 mL of pyridine. The crude is purified by vacuum flash chromatography (heptane) to give 2.10 g of a colorless oil in 72.2% yield.

EXAMPLE 11
1-Phenoxy-2,2,6,6-tetramethylpiperidine (1.0 Mole % Phosphomolydbic Acid Hydrate Based Nitroxyl; 2 Molar Excess Aniline)

The procedure of Example 5 is repeated using 1.95 g (12.5 mmol) of 2,2,6,6-tetramethylpiperidine-1-oxyl, 3.09 g (30.0 mmol) of tert-butylnitrite and 228 mg (~0.125 mmol) of phosphomolydbic acid hydrate ($H_3PMo_{12}O_{40}$) in 100 mL of pyridine and 2.32 g (25 mmol) of aniline in 5 mL of pyridine. The crude is purified by vacuum flash chromatography (heptane) to give 2.0 g of a colorless oil in 68.7% yield.

What is claimed is:

1. A process for preparing a sterically hindered N-aryloxyamine of formula I, II, III, IV, V or VI

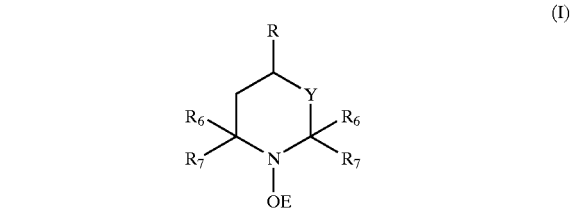

(I)

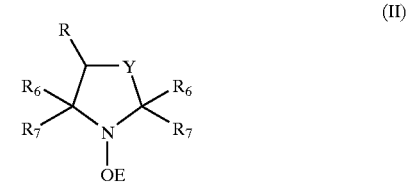

(II)

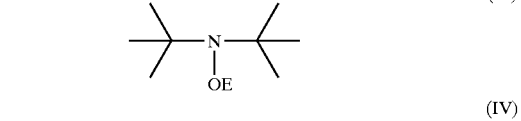

(III)

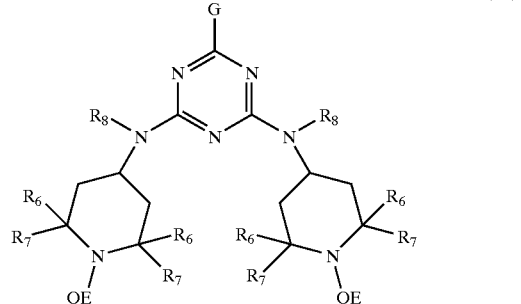

(IV)

(V)
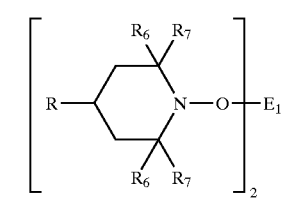
(VI)
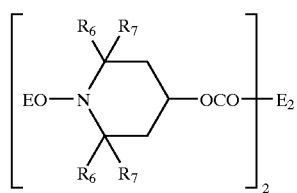
which process comprises
  reacting a sterically hindered nitroxyl compound of formula VII, VIII, IX, X or XI
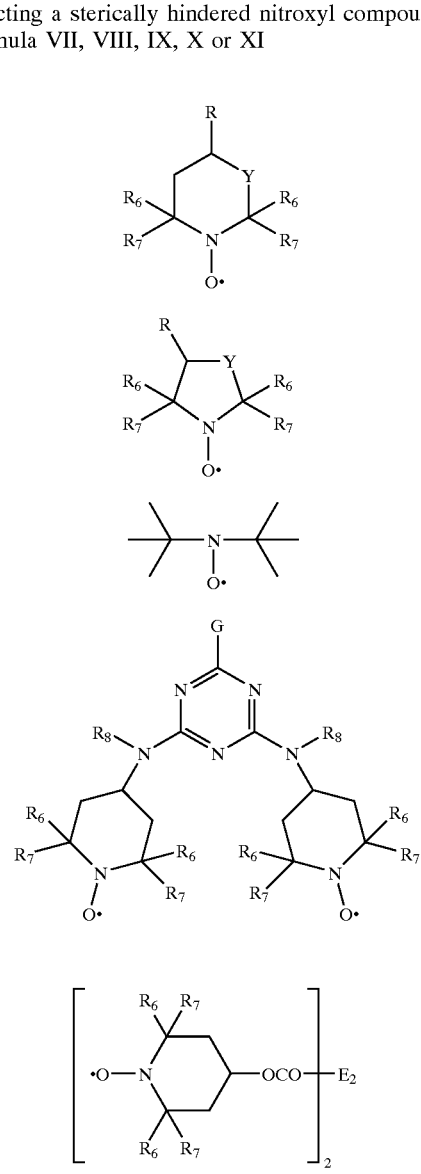
with a diazonium salt of an aromatic amine of formula XII, XIII or XIV
(XII)
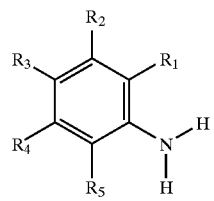
(XIII)
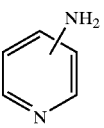
(XIV)
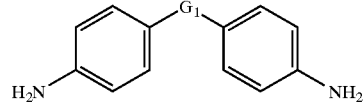
in the presence of a polyoxometalate of formula (1) or (2)
(1)
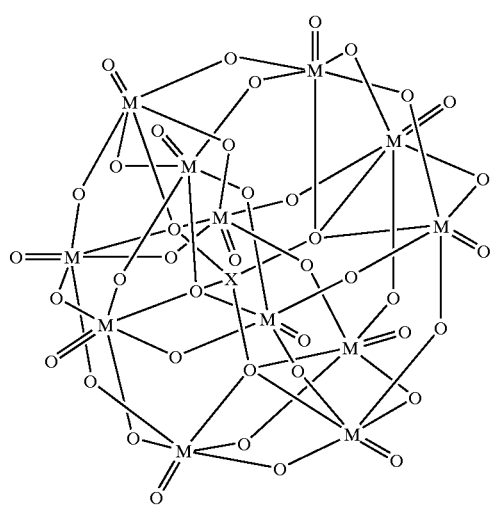
(2)
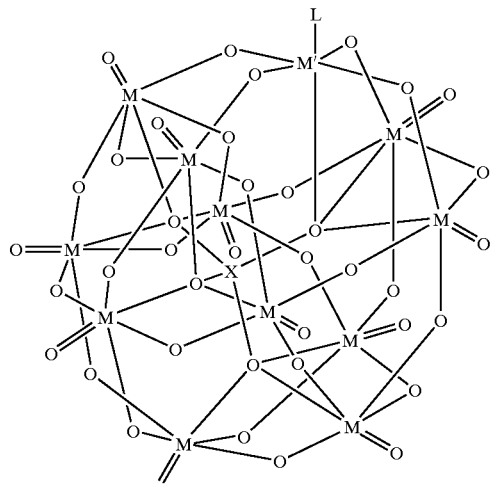
where
  M is W(VI) or Mo(VI); or each M is independently selected from W(VI), Mo(VI), V(V), Nb(V) and Ta(V);

L is water;

X is P, Si, Sn, Ge, As, B, Al, Zn, Co or Fe;

M' is a transition metal of Group 4, 5, 6, 7, 8, 9, 10, 11 or 12, or is a metaloid selected from Al, Si, Ga, Ge, Sn, Sb, Te and Pb; and Y is —$CH_2$—, —O—, —S— or —$NR_8$— where $R_8$ is hydrogen or alkyl of 1 to 12 carbon atoms, $R_6$ and $R_7$ are independently alkyl of 1 to 8 carbon atoms, or $R_6$ and $R_7$ together are tetramethylene or pentamethylene, E is 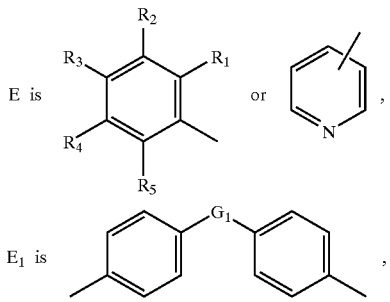

$E_2$ is alkylene of 2 to 12 carbon atoms,

G is chloro or —N(2-ethylhexyl)$_2$, $G_1$ is —$CH_2$—, —CO— or —O—,

R is hydrogen, alkyl of 1 to 18 carbon atoms, aralkyl of 7 to 15 carbon atoms, aryl of 6 to 10 carbon atoms, hydroxyl, carboxyl, amino, alkylamino of 1 to 18 carbon atoms, dialkylamino of 2 to 36 carbon atoms, oxo, alkylthio of 1 to 18 carbon atoms, alkoxy of 1 to 18 carbon atoms, aryloxy of 7 to 15 carbon atoms, benzoyloxy, alkylcarbonyloxy of 2 to 18 carbon atoms or alkylcarbonylamino of 2 to 18 carbon atoms, and $R_1$ to $R_5$ are independently hydrogen, halogen, nitro, cyano, alkyl of 1 to 18 carbon atoms, aralkyl of 7 to 15 carbon atoms, aryl of 6 to 10 carbon atoms, hydroxyl, carboxyl, alkylthio of 1 to 18 carbon atoms, alkoxy of 1 to 18 carbon atoms, aryloxy of 7 to 15 carbon atoms, alkylcarbonyloxy of 1 to 18 carbon atoms, alkylsulfonyl of 1 to 18 carbon atoms, arylsulfonyl of 6 to 15 carbon atoms, sulfo or —P(O)(OH)$_2$ or —P(O)(O$R_6$)$_2$, or any two vicinal substituents connected together to form a mono or polycyclic ring, so that formula VII can represent inter alia 1-naphthylamine or 2-naphthylamine; or any two vicinal carboxyl groups can be joined to form an imide; or $R_3$ is 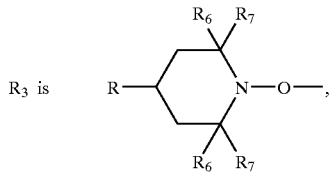

where R, $R_6$ and $R_7$ are as defined above.

2. A process according to claim 1 wherein M' is a metal of Group 4, 5, 6, 7, 8, 9 or 10 of the periodic table.

3. A process according to claim 1 wherein

M is W(VI) or Mo(VI);

L is water;

X is P; and

M' is Ti, Cr, Mn, Fe, Co, Cu, Ni, Zn, Ru, Rh, Pd, Ag, Re, Os, Ir, Pt, Au, Hg, Al, Sn or Pb.

4. A process according to claim 1 wherein M' is iron(II).

5. A process according to claim 1 wherein M' is cobalt(II).

6. A process according to claim 1 wherein M' is copper (II).

7. A process according to claim 1 wherein M' is vanadium (V).

8. A process according to claim 1 wherein M is a combination of metals selected from W(VI), Mo(VI), V(V), Nb(V) and Ta(V).

9. A process according to claim 1 in which X is a metaloid selected from B, Sn, Ge, As and Si.

10. A process according to claim 1 which is performed at a temperature of between about 20 and about 70° C.

11. A process according to claim 1 which is performed in the presence of pyridine.

12. A process according to claim 1 which is carried out in the presence of about 0.1 mole percent to about stoichiometric quantities of the polyoxometalate.

13. A process according to claim 1 which is carried out in the presence of about 2 mole percent to about stoichiometric quantities of polyoxometalate.

* * * * *